United States Statutory Invention Registration [19]

[11] Reg. Number: H958

DeVita, Jr. et al. [43] Published: Aug. 6, 1991

[54] PDQ CANCER TREATMENT INFORMATION SYSTEM

[75] Inventors: Vincent T. DeVita, Jr.; Susan M. Hubbard, both of Bethesda, Md.

[73] Assignee: The United States of America as represented by the Secretary of the Department of Health and Human Services, Washington, D.C.

[21] Appl. No.: 556,420

[22] Filed: Jul. 24, 1990

[51] Int. Cl.[5] ..... G06F 15/00

[52] U.S. Cl. ..... 364/413.02

[56] References Cited

PUBLICATIONS

Hubbard et al, "A Computer Data Base for Information on Cancer Treatment", *The New England Journal of Medicine,* Feb. 5, '87, pp. 315–318.

Hubbard et al, "PDQ:An Innovation in Information Dissemination Linking Cancer Research and Clinical Practice," *Important Advances in Oncology,* 1987, pp. 263–277.

*Primary Examiner*—Linda J. Wallace

*Attorney, Agent, or Firm*—Birch, Stewart, Kolasch & Birch

[57] ABSTRACT

The Physician Data Query (PDQ) System is a clinically oriented computer data base developed to make recent information on cancer treatment widely available to the medical community. It represents an effort to promote diffusion of information about the treatment of cancer throughout the country, facilitates access to clinical trials, and accelerates the practical application of advances in research. The computer system provides information about state-of-the-art cancer treatment which is updated monthly by an editorial board. It also includes a file of active cancer-research protocols and directory of physicians and organizations providing cancer care to which physicians can gain access by geographic location. The PDQ system provides a search and display method in a simple menu driven process. Transmission of information about cancer over commercial telecommunication networks gives professionals easy access to the system through individual computer terminals.

1 Claim, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PDQ CANCER TREATMENT INFORMATION SYSTEM

The present invention is directed to an information dissemination system and method for accessing information which links cancer research and clinical practice. The PDQ (Physician Data Query) Cancer Treatment Information System supplies physicians with up-to-date information on cancer treatment resources and other information, and makes such information widely and readily available. This system creates a method for accessing medical information which involves a user-friendly menu driven interface to allow users to search and display information without learning a specialized search language. Thus, current information relating to a specific type of cancer is readily and easily accessible to a plurality of independent physicians.

BACKGROUND OF THE INVENTION

Following the passage of the National Cancer Act, the National Cancer Program, in addition to funding basic research, supported the training of cancer specialists and established a network of academic and community-based cancer centers. In 1973, the first specialty boards in medical oncology were administered. By 1980, the number of medical and radiation oncologists had increased from a few hundred specialists to several thousand. Further, by 1980, it had become evident the national mortality rate for a number of advanced, formerly fatal cancers, was beginning to fall as new and effective treatment regimes were being incorporated into the care of patients with these diseases, at the community level. Institutes ' (NCIs') programs, which monitor cancer Five year survival data from the National Cancer incidents survival in twelve percent of the U.S. Population, indicated that survival for all patients diagnosed with serious visceral cancer had increased from 38% in 1963 to 48% in 1980. Striking changes in survival were being documented in patients with a number of disseminated cancers such as acute lymphocytic leukemia, Hodgkin's disease, soft-tissue sarcoma, testicular cancer, and a variety of other pediatric neoplasms in which major breakthroughs in treatment had occurred, as well as in women with breast cancer following adjuvant therapy. While survival data provided gratifying evidence that substantial progress against cancer had been made, they also emphasized that a five to ten year lag existed between the identification of a curative therapy and its acceptance by the medical community and widespread application in patient care. This clearly suggested that significant increases in patient survival could be achieved with a wider and more rapid dissemination on information effective treatments.

A unique feature of the National Cancer Act of 1971 was a provision that enabled the NCI to establish a National Network of resources that would facilitate the development of effective methods to prevent, diagnose, and treat cancer. In addition, the Act gave NCI responsibility for developing new improved methods to disseminate information on advances in cancer research. However, the act included the words "insofar as feasible" in its language and indicated that the Congress clearly recognize that there were obstacles in 1971 limiting the Institutes' ability to fulfill the mandate. For example, there were few trained medical radiation and pediatric oncologists either at academic institutions or in private practice to care for cancer patients and develop or deliver effective cancer treatments. There was a critical need for a network of institutions specializing in cancer care where physicians could send patients so that they would not have to travel great distances for treatment. For these reasons, the Congress gave special resources to NCI to develop treatment resources throughout the country and an information dissemination program to make the most current information on progress against cancer readily available.

Thereafter, an International Cancer Research Databank (ICRDB) was created to foster the rapid and effective exchange of information on cancer research throughout the world. NCI surveyed an international group of 250 basic scientists and clinical investigators in an attempt to define what services would best meet the needs of the international cancer research community. The Institute decided to build its new information program using computers so that the information could be updated and enhanced over time The NCI developed CANCERLINE databases. These updatable files resided in machine-readible form in the memory of a central computer which could be accessed by computers with software that communicated with the central computer.

The first on-line information system, developed by the ICRDB program, was a bibliographic database called CANCERLIT, which was created in 1974. The data base was composed of 42,000 citations taken from Carcinogenesis Abstracts and Cancer Therapy Abstracts, two abstract journals of the mid-1970s NCI then made CANCERLIT widely available to the medical and scientific community over the National Library of Medicine (NLM) computer system and searchable within a command language used by the Medical Literature Analysis and Retrieval System (MEDLARS) databases. In an attempt to ensure CANCERLIT as a comprehensive resource, many books and journals were screened, indexed and abstracted However, the CANCERLIT database did not provide information on research in progress.

NCI then developed, through their staff of the ICRDB, a new computerized database called CLINPROT (Clinical Protocol), to disseminate information on investigational treatment protocols supported by NCI. Each CLINPROT record was created using full clinical research protocol as the source document. Protocol summaries of 1000 to 5000 words were constructed, with special index terms that allowed users to receive protocols by tumor type and treatment. CLINPROT also used the specialized command language of the MEDLARS database While the CLINPROT database added a new dimension to research information, collective and disseminated, by the NCI, the protocol summaries were not indexed by stage, histolic type, or participating investigators and institutions. Therefore, it was difficult for physicians to identify clinical trials appropriate for cancer patients that were being conducted in a particular location. Further, CLINPROT did rot provide information on state-of-the-art treatment CLINPROT merely served as an on-line catalogue on clinical research that provided physicians who were designating treatment protocols with information on research performed by others, thereby minimizing duplication of effort. Further, as with all MEDLARS databases, effective information retrievals from CLINPROT required knowledge of the NLM's specialized searching language.

SUMMARY OF THE INVENTION

The present invention is directed to a system and method which solves the above-mentioned deficiencies known to have existed in the prior systems. The PDQ cancer treatment information system is a clinically-oriented system developed to make recent information on cancer treatment widely available to the medical community. It represents an effort by the NCI to promote diffusion of information about the treatment of cancer throughout the country, facilitate access to clinical trials, and accelerate the practical application of advances in research.

The computer system provides information about state-of-the-art cancer treatment, which is updated monthly by an editorial board. It also includes a file of active cancer-research protocols and a directory of physicians and organizations providing cancer care to which physicians can gain access by geographical location, as well by other means.

PDQ was designed for physicians who may not be familiar with computers to permit them to search for, and display information, without learning a specialized search language. PDQ utilizes a computer mainframe, which allows a large amount of data to be stored and made available to physicians rapidly and accurately. Transmission or information about cancer over commercial telecommunication networks gives health professionals access to PDQ by means of a computer terminal and local telephone lines.

Since a major goal was to provide up-to-date information on treatment research, the PDQ system was also designed to provide explicit, clinically relevant information about research in progress, directing Physicians to open clinical trials if no effective therapy existed. To ensure that PDQ is a comprehensive source of information about ongoing clinical trials, all active Protocol supported by the NCI are automatically abstracted and entered into the system. In addition, clinical trials being performed without such support are solicited for inclusion in PDQ. At any time, the PDQ protocol file contains approximately 1000 treatment protocols, twenty Percent of which have been voluntarily submitted. Each protocol is indexed according to disease and stage-specific eligibility criteria, as well as details of treatment, to allow users to narrow down geographically classified information on participating investigators. Thus, physicians can easily retrieve names, addresses, and telephone numbers of clinical investigators according to location.

Further, PDQ's physician directory contains information of more than 12,000 physicians and has an electronic computation of the membership directories of seventeen professional societies established for physicians who treat cancer. Clinical investigators whose protocols are supported by the NCI, as well as those who are voluntarily submitted protocols that have been accepted by the editorial board for inclusion in the PDQ protocol file, are also listed in the PDQ directory. Each Physician's record includes his or her full name, address, telephone number, medical specialties, and organizational affiliations.

Still further, a directory of organizations with programs of cancer care has been assembled. Also, because all physicians may not be familiar with searching on computer systems, the PDQ software is designed to guide them through the data and allow them to retrieve information for more than one file by means of a series of simple "menus" and commands. These menus replace the difficult specialized searching language of the prior systems. A main menu allows physicians to chose from among the following: a general description of the PDQ, instructions for searching, a news file, the membership of the PDQ editorial board, or one of the data files (cancer treatment information, the directory of physicians and organizations, or the protocol file) Menus in each file guide physicians to the information that they seek, and from a technical viewpoint, allow the software to map and retrieve information from multiple data files in a manner that is transparent to users. Further, experienced users can bypass menus by entering a string of menu selections.

OBJECT OF THE INVENTION

It is therefore an object of the present invention to create a computerized system which makes up to date information on state-of-the-art cancer treatment widely and readily available.

It is a further object of the invention to provide an on-line source of geographically matrixed information on active research protocols and a directory of physicians and organization to provide cancer care.

It is a further object of the invention to create a system which users can identify the full range of treatment alternatives for all major cancers, locate clinical trials for patients, and identify physicians and treatment facilities for consultation and referral It is a still further object of the invention to create a medical information system to integrate divergent data files (state-of-the-art treatment, protocols, medical literature, and directory information) by using a user-friendly interface that permits retrieval of information across the files in a manner that is "transparent" to users and does not require the use of a structured search language.

It is a still further object of the invention to create cancer information files which contain treatment summaries that synopsis state-of-the-art therapy for all major cancers by providing current data on prognosis, relevant staging, histolic classifications, therapies that constitute the standard of care, and references to key literature.

Finally, it is an object of the invention to create a protocol file containing over 1000 clinical trials which compliment the cancer information file, with each protocol summary describing the study objectives and being indexed by disease and stage-specific eligibility criteria.

These and further objects of the present invention will become more readily apparent from their understanding of the preferred embodiments described below with reference to the following drawing figures

BRIEF DESCRIPTION OF THE DRAWINGS

The present invention will become more fully understood from the detailed description given hereinbelow and the accompanying drawings which are given by way of illustration only and are not intended to limit the present invention, and wherein:

FIG. 1(*b*) illustrates a personal computer with a keyboard and display;

The above-mentioned drawing will be described in detail in the following detailed description.

DETAILED DESCRIPTION OF THE EMBODIMENT

Figure 1A:
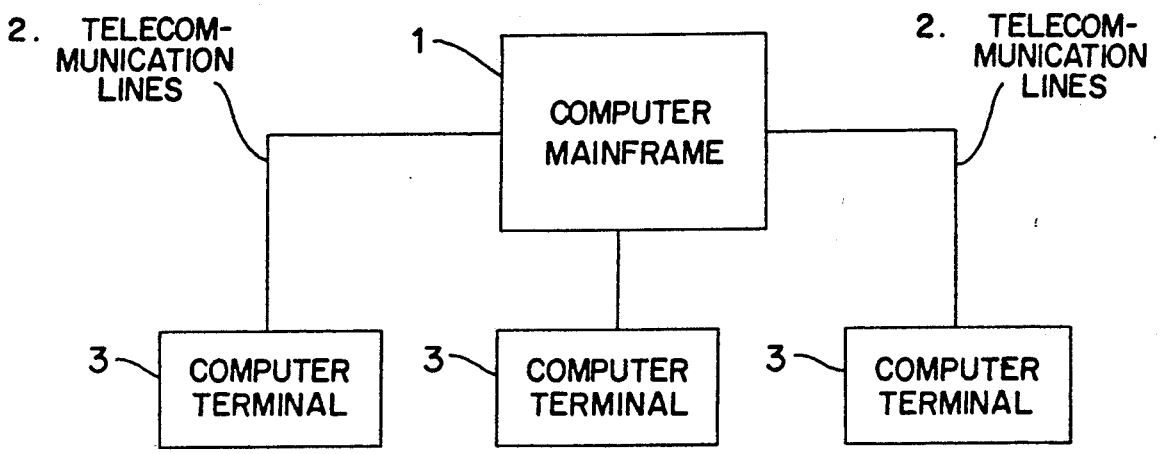
FIG. 1(*a*) illustrates the PDQ system for dissemination of information.
Figure 1B:
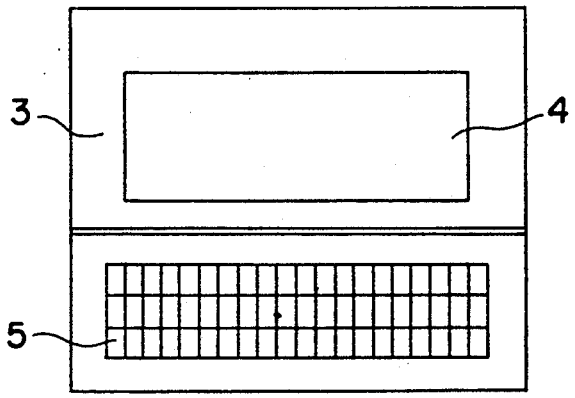

FIG. 1(*a*) illustrates the Physician Data Query (PDQ) information dissemination system. The system is a computer based system which makes information about state-of-the-art cancer treatment widely available to the medical community. PDQ uses a computer mainframe (1), which allows a large amount of data to be stored and made available to physicians rapidly and accurately. Transmission of information about cancer treatment over commercial telecommunications lines (2), gives health Professionals access to PDQ by use of a computer terminal (3) hooked into the lines (2).

Because it is increasingly difficult to keep abreast of the new developments in cancer therapy, PDQ is a valuable resource for all clinicians, or those trained as cancer specialists. Information in PDQ assists the physicians and other health professionals to identify and replace knowledge that has become outdated or obsolete. State-of-the-art statements provide a succinct overview of current data on prognosis, staging, and stage specific treatment options that can guide patient care and facilitate the selection of an optimal treatment plan for patients with cancer. Citations included in each section of the state-of-the-art statements provide key references from scientific literature that support the use of the therapy as a standard or investigational treatment in patients with that type and stage of cancer. Information for patients concisely describes the prognosis, staging, classification, and treatment options in simple, easily understood terms that facilitate its use as an educational research for patients and their families during the diagnostic evaluation when treatment decisions must be made.

The PDQ system is an on-line data base system which uses computer technology to maintain the currency of information in the system. Thus, information from the extramural community on the medical content on the state-of-the-art statements is continually maintained in a computer mainframe (1). In maintaining the currency of the cancer information file, an editorial board constantly reviews voluntary protocol submissions, and the development of new state-of-the-art statements. The board further reviews information in a monthly basis from treatment literature, proposed modifications to PDQ statements, and needs to prepare additional state-of-the-art statements to enhance the file of the mainframe (1). New literature citations to support modifications cf statements are regularly added. Further, directories for the physicians and organizations also have their files maintained. Thus, accurate information is constantly input to the PDQ system on protocols, physicians and organizations.

The on-line system of PDQ allows Physicians to obtain access to state-of-the-art information by merely utilizing a small computer terminal (3). FIG. 1(*b*) shows such a terminal which includes a keyboard (5) and a display screen (4). A physician need only connect to the system through local telecommunication lines and access it through his computer screen (4). The PDQ system is one which is user-friendly and continually prompts a user through a series of menus which lead him to his desired information. By merely choosing one of a plurality of options from a menu displayed on a display screen (4), and inputting a corresponding numerical value through the keyboard (5), the PDQ system will guide any physician to information on state-of-the-art cancer treatment.

Table 1 illustrates the PDQ main menu, which is displayed on a display screen (4) of a user's terminal (3), upon accessing the PDQ system. The PDQ system is one which is completely menu-driven. The system provides information about state-of-the-art cancer treatment which is updated monthly by an editorial board. The main menu, when prompted by the user, allows the user to select a number, from those shown on the main menu in Table 1, to retrieve one of a plurality of options.

The PDQ searching system was designed to guide users through data and allow them to retrieve information from more than one file by means of a series of simple menus and commands. The "main menu" as shown in Table 1, allows physicians to choose from among the following: (1) a general description of the PDQ system; (2) instructions for searching; (3) a news file; (8) the membership of the PDQ editorial board; or (4) through (7), one of the existing data files (for cancer information, the directory of physicians, the directory of organizations, or the protocol file). Further, (9) is directed to a means exiting the PDQ system.

Menus in each file guide physicians to the information that they seek and, from a technical viewpoint, allow software of the PDQ system to map and retrieve information from multiple data files in a manner that is transparent to users. Further, experienced users can bypass menus by entering a string of menu selections (command "stacking" to be described hereinafter). In addition, by entering simple commands, users can easily return to previous menus and change files at will.

Figure 2:
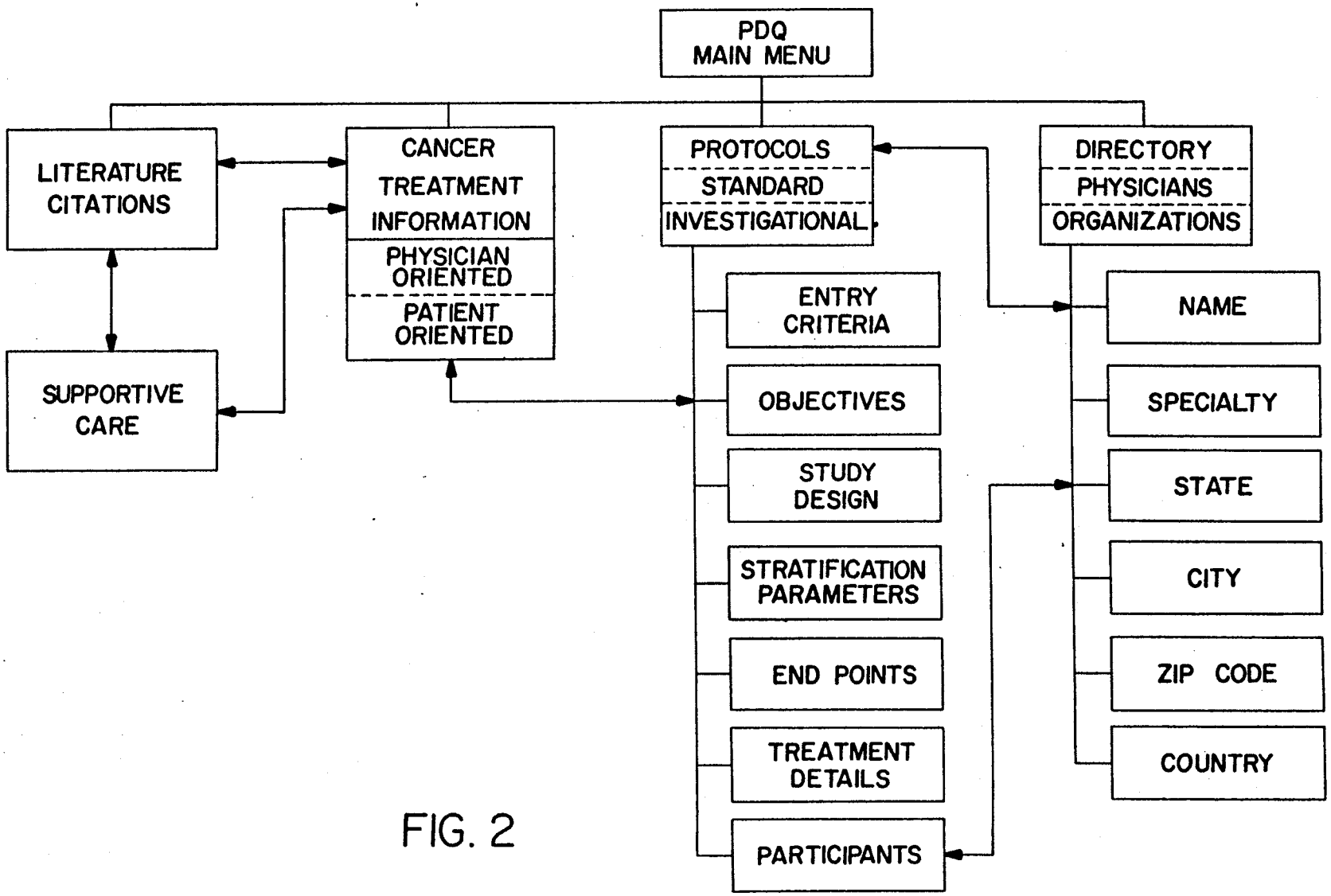
FIG. 2 illustrates a flowchart of the PDQ Main Menu for accessing the plurality of data files.

The PDQ main menu has a plurality of features, as described previously with regard to Table 1, but is mainly directed to providing a user with a selection of one or more various data files. These data files are shown in FIG. 2, for example, which illustrates a flow chart for retrieving information from each of the plurality of data files. The files include the directory files, for either physicians or organizations, and cancer treatment information files for listing information or obtaining cancer treatment by body location or a specific cancer type. Further, a list of literary citations is also included in which the PDQ system maintains information in the cancer-information file which contains abstracts of literature cited.

Next, a description of how the retrieval method of the PDQ system operates to retrieve information from the various data files, will be given.

Initially, a physician will make a selection as to which of the various data files he wishes to access based on data obtained from a prospective patient. This patient data then directs the physician in selecting corresponding data file numbers from the displayed PDQ main menu, as shown in Table 1. The selected number is then input through the terminal keyboard (5). For example, a physician may desire to retrieve information on colon cancer based on data from a prospective patient. To obtain information with which to treat a prospective patient, the physician initially selects the cancer information data file from the displayed PDQ main menu, by entering "4" into the system. This selection from the main menu, when entered, then prompts the display of a secondary menu. This allows the physician who chooses the cancer information file, to select one or more options from a series of multiple menus based on prospective patient data.

TABLE 1

| PDQ MENU | |
|---|---|
| The following information is available in the PDQ Retrieval System: | |
| 1 Description | 5 Physicians |
| 2 Instructions | 6 Organizations |
| 3 News | 7 Protocols |
| 4 Cancer Information | 8 PDQ Editorial Board |
| 9 Exit PDQ | |

Once the physician (hereinafter referred to as the user) selects the cancer information file, a diagnosis selection menu is then displayed, as shown in Table 2. The diagnosis selection menu allows retrieval of cancer information by accessing one of three categories. The user may retrieve the information by body system or site, by selecting 1; by histolic tissue or type, by selecting 2; or by childhood cancer, by selecting 3, based on known prospective patient data. This allows the user to, by a selection from a sequential set of menus, access information on a specific type of cancer, though the specific type of cancer in a patient may not be known. For example, if the user knows the area of the patient's body in which the cancer is present, he merely selects the first category, "By Body System or Site".

TABLE 2

| DIAGNOSIS SELECTION |
|---|
| 1 By Body System/Site |
| 2 By Histologic Tissue/Type |
| 3 By Childhood Cancer |

Once the category of "By Body System or Site", has been chosen from the diagnosis selection menu and entered, a diagnosis selection by body system or site menu is then prompted, as shown in Table 3. This allows the user to then select the particular body system or site which corresponds to cancer information desired to be retrieved to treat a prospective patient. The user can then select the particular body system or site associated with the cancer, and can thus obtain accurate information based on the body system or site of the cancer.

TABLE 3

| DIAGNOSIS SELECTION BY BODY SYSTEM/SITE |
|---|
| 1 Acquired Immune Deficiency Syndrome (AIDS) |
| 2 Skin |
| 3 Eye |
| 4 Head and Neck |
| 5 Thorax/Respiratory |
| 6 Digestive/Gastrointestinal |
| 7 Kidney/Urinary |
| 8 Musculoskeletal |
| 9 Hernatological |
| 10 Endocrine |
| 11 Male Reproductive |
| 12 Female Reproductive |
| 13 Breast |
| 14 Neurological |

Upon the user selecting "Digestive or Gastrointestinal", by entering a 6 into the system, a category specific menu on cancer in that area of the body will then be prompted. As shown in Table 4, for example, a category specific digestive/gastrointestinal cancer menu has been prompted and displayed. This menu is one in a series of menus directing the user to a specific type of cancer in a step-by-step process. As previously described, if the user desires selecting information on colon cancer for patient treatment, he can be directed to such information by the above-mentioned series of menus Finally, upon reaching the digestive/gastrointestinal cancer menu, he can select number 9 for colon cancer.

TABLE 4

| DIGESTIVE/GASTROINTESTINAL CANCER |
|---|
| 1 Esophagus |
| 2 Stomach |
| 3 Liver and Intrahepatic Biliary Tract |
| 4 Gallbladder |
| 5 Extrahelatic Biliary |
| 6 Pancreatic (exocrine) |
| 7 Small intestine |
| 8 Gastrointestinal Carcinoid Tumor |
| 9 Colon |
| 10 Rectum |
| 11 Anal |

Upon selecting the appropriate type of cancer for which information is desired, the cancer information menu on colon cancer, as shown in Table 5, will be displayed. This is a menu which directs the user to all the available categories of information concerning a specific type of cancer. Prognostic and treatment information contained in "state-of-the-art" statements and the "information for patients" sections are selectable from a menu that is dynamically generated when the user selects a particular cancer to be diagnosed. The user can obtain information for determining what a particular state a patient's specific type of cancer may be in, and general treatment information options for that state. Further, state-of-the-art prognosis information is available as is information, once a particular stage of the cancer has been diagnosed, on treatment of a patient with cancer in that particular stage. Thus, a prospective patient can be treated in accordance with the diagnosis information obtained. Also stage-specific treatment option selection also concludes with a statement on the number of protocols that are currently in the PDQ protocol file which are indexed for that stage.

TABLE 5

| CANCER INFORMATION MENU | |
|---|---|
| COLON CANCER | |
| Patient Education | State-of-the-Art Information |
| 1 Prognostic Statement | 4 Prognosis |
| 2 Stage Explanations | 5 Cellular Classification |
| 3 General Treatment Options | 6 Stage Information |
| | 7 Treatment by Cell Type/Stage |
| 8 Display All Information | |
| 9 Continuation Options to Select Physicians, Organizations, or Protocols | |

Further, PDQ also provides a continuation option to make it convenient for users to move from the cancer information file to other files. A list of the continuation options, for a user who selects information on colon cancer, is shown in Table 6. Thus, the user can jump from the cancer information file to one which lists the directory of physicians, organizations, or to a list of protocols to further aid in patient treatment.

TABLE 6

| CONTINUATION OPTIONS |
|---|
| COLON CANCER |
| The following options are available for continuing your search. |
| Your cancer diagnosis will be used automatically if you choose option 3 for protocol retrieval. |
| 1 Physicians |
| 2 Organizations |

TABLE 6-continued

| 3 Protocols |
|---|

Throughout the PDQ search, users may elect to return to a previous menu, change files, restart from the PDQ main menu, or exit from PDQ by entering a simple command. In addition, command stacking in all PDQ files allows experienced searchers to bypass menus at most prompts by entering a string of commands that are formulated into a query by the retrieval software.

For example, the user, who is familiar with the system, can access information on colon cancer merely by entering the search term "colon" or the first few letters of the diagnostic with a truncation system (:) at the prompt. Therefore, with this term entered into the system, the PDQ system will then skip many of the intermediate menus, and display only the cancer information menu. Thus, the user can obtain information quickly on a specific type of cancer. However, the main emphasis of the PDQ system is designed to allows users who are not extremely familiar with the system to obtain information in a step-by-step menu driven process. Further, it allows the user to obtain information based on a specific type of diagnosis selection as shown in FIG. 4, when he is unsure of the specifics of the cancer.

The PDQ system also allows users to obtain information from various directory data files listing various physicians and organizations throughout the country. The physician directory, as shown in Table 7, currently contains information on more than eleven thousand physicians who devote a major portion of their clinical practice to treatment of cancer patients. The directory is an electronic compilation of the membership directories of sixteen national medical societies established for physicians who treat cancer. The societies have listed their physician members in the PDQ files. Clinical investigators whose protocols have been supported by NCI, as well as those who voluntarily submitted protocols that have been accepted by the PDQ editorial board for inclusion in the PDQ protocol file, are also listed in the PDQ directory. Each physician's record includes his full name, address, telephone number, medical specialities, and organizational affiliations.

Users can retrieve information about physicians by entering one of the following: 1, the physician's name; 2, a medical specialty; and 3-6, a particular geographic location. This PDQ physician retrieval menu, as previously described, is shown in Table 7. Once an individual physician or subset of physicians is defined, users are offered a variety of print/display options that enable them to review the retrieval records in varying degrees of detail. Treatment protocols for which a physician is a principal investigator can also be retrieved, since the PDQ system automatically links the physician record to the appropriate records and other data files.

TABLE 7

| PDQ PHYSICIAN RETRIEVAL<br>You may narrow set of physicians by |
|---|
| 1 Physician Name |
| 2 Medical Specialty |
| 3 State |
| 4 City |
| 5 Zip Code |
| 6 Non-U.S. Country |

Similar to the physician directory, there is also an organization directory. The organization directory includes information on more than fourteen hundred health care organizations and institutions at which the NCI supports clinical treatment and hospitals with established cancer programs. Information on organizations can also be retrieved by name or by specific geographic location using state, city, or zip code. Each organization record includes the address, telephone number, and name of a person at the institution who has agreed to serve as the PDQ contact and can answer questions about the organization's cancer treatment program and facilities. As in the physician's directory, PDQ uses file-to-file linkages to automatically display all active protocols for a specific organization if requested by the user.

A final data file which exists is the protocol file. The protocol file currently contains information on more than one thousand active treatment protocols being conducted in the United States. All active treatment protocols directly supported by the NCI are automatically summarized and entered. Further, twenty percent of the protocols have been voluntarily submitted for inclusion into the PDQ system. Protocols can be retrieved by diagnosis, stage, identification number, treatment modelity, key words from the protocol title, and location using one or more state postal codes. This protocol retrieval process can be seen, for example, in Table 8.

TABLE 8

| PDQ PROTOCOL RETRIEVAL |
|---|
| 2 protocols retrieved |
| DIAGNOSIS = BREAST CANCER |
| STAGE = STAGE II |
| KEYWORD(S) = POSTOPERATIVE |
| PHASE(S) = PHASE III |
| MODALITY = RADIATION AND CHEMOTHERAPY |
| STATE = NY.NJ.CT |
| You may narrow set of protocols by |
| 1 ID Number |
| 2 Cancer Diagnosis |
| (use NARROW to decrease number of protocols) |
| 3 State of Disease |
| 4 Phase of Protocol |
| 5 Treatment Modality |
| 6 Drug Name |
| 7 State |
| or you may |
| 8 Erase Existing Selection Criteria |
| 9 Display Current Set of Protocols |

Each protocol record includes details description of the objectives of the study, patient eligibility requirements, description of the treatment regime, details about dose and schedule of the administration, and information about who is performing the clinical trial and where it is being conducted.

The PDQ Protocol file can be accessed in a plurality of ways. The user may select the protocols for a particular cancer diagnosis and stage by choosing the continuation option on the cancer information menu for that diagnosis, as previously described. This option enables the user to carry a search from the cancer information file into the protocol file. All of the clinical files that accept patients with that stage or cell type of cancer are automatically retrieved from the PDQ protocol file without reformulating the search statement.

Users may further select protocols as a primary retrieval option from the PDQ main menu. When this option is used, a menu is presented that enables users to select protocols by cancer diagnosis, stage, drug, treatment modelity, key words in the protocol title, phase of clinical investigation, or any combination of these parameters to generate a list of protocols accepting patients which meet the search criteria. Every protocol that is being conducted, within the parameters that have been specified, may be retrieved and reviewed, or the user may narrow the retrieval protocols to one or more states, to select only those that are being conducted in a specific location.

Each time a protocol set is defined, PDQ informs the user how many protocols, meeting the search criteria, have been retrieved. At any point, the user may either redefine the search criteria or decide to display and Print protocol information in varying degrees of detail by selecting one of the print display options. These various print display options are shown in Table 7. These commands allows the user to print as little as a listing of protocol titles or as much as entire protocol summaries with listing of all participating investigators. Users can also customize their own print/display format from a menu containing all protocol elements.

TABLE 9

| PROTOCOL DISPLAY OPTIONS | |
|---|---|
| 1 BROWSE | Through protocol titles with option to select one or more protocols for display. |
| 2 SHORT | Display all protocols in short format. |
| 3 MEDium | Display all protocols in medium format. |
| 4 NAMES | Display all protocols and investigators. |
| 5 LONG | Display all protocols in long format. |
| 6 CUSTom | Display all protocols in custom format. |
| 7 Return | To protocol menu. |

. . . . . .

| HELP SCREEN | |
|---|---|
| Format | Function |
| BROWSE | Display protocol names and id-numbers with option to select one or more for deferred printing in short, medium name or long format. |
| SHORT | Display protocol id-number, name and protocol chairman name and address for all retrieved protocols. |
| MED | Display same information as short format plus protcol entry criteria and objectives. |
| NAMES | Display same information as medium format plus name and address information for protocol investigators. |
| LONG | Display all protocol information for all retrieved protocols. |
| CUST | Display selected information for all retrieved protocols, in user defined order. |

Shortcut: to bypass the protocol print menu FROM THE PROTCOL SELECTION MENU, type the key word associated with the desired format, e.g., BROWSE, SHORT, MED, or LONG A list of protocol data elements is shown in Table 10. These elements include objectives, entry criteria, warnings, and a plurality of others as shown in Table 10. Users can select any number of items, in any order, and can maintain their customized print format for an entire search session or redefine a format at will.

TABLE 10

| PROTOCOL DATA ELEMENTS |
|---|
| 1 Objectives |
| 2 Entry Criteria |
| 3 Warning |
| 4 Outline |
| 5 Stratification |
| 6 Special Study Parameters |
| 7 End Points |
| 8 Projected Accrual |
| 9 Dosage Schedule |
| 10 Dosage Forms |
| 11 Participants |

The PDQ protocol file provides up-to-date information on investigational treatment options, that is especially valuable to clinicians when no effective standard therapy exists and patients should be offered investigational therapies. Because protocol retrievals can be tailored to specific clinical situations, PDQ can perform a physician with a "snapshot" of clinical research being conducted in that disease which can then be narrowed to a "closeup" of those being conducted and specific location. This enables physicians to identify appropriate clinical trials with knowledgeable investigators who can be conducted for consultation or referral.

The PDQ directory file of physicians and organizations provides an electronic telephone book of clinical resources that enhances communication among cancer care providers. The ability to retrieve directory information by city, state or zip code can facilitate the rapid identification of treatment resources that are available for patients in a specific geographical area.

Through the use of the PDQ cancer treatment system, a physician can obtain appropriate information to treat a cancer patient. State-of-the-art information is made readily available and easily accessible to all physicians. Further, information on local expert physicians or organizations may be obtained to aid in obtaining treatment information. Thus, PDQ disseminates up-to-date cancer treatment throughout the medical community.

From the above-described embodiments of the present invention, it is apparent that the present invention may be modified as would occur to one of ordinary skill in the art without department from the spirit and scope of the present invention which should be defined solely by the appendent claims. Changes and modifications of the system contemplated by the present preferred embodiments will be apparent to one of ordinary skill in the art.

What is claimed is:

1. A method of accessing medical information, relating to cancer, for cancer treatment of a prospective patient, comprising the steps of:

a) obtaining data describing a prospective patient;

b) displaying a first menu of a plurality of types of information;

c) selecting an information type from said first menu relating to a type of information, based on said prospective patient data;

d) displaying a second menu of a plurality of diagnosis sections relating to said selected information type;

e) selecting a diagnosis selection from said second menu relating to a type of diagnosis, based on said prospective patient data;

f) displaying a third menu of a plurality of body-area categories relating to said selected diagnosis;

g) selecting a body-area category from said third menu relating to an area of the prospective patient's body, corresponding to said selected diagnosis type, based on said prospective patient data;

h) displaying a fourth menu of a plurality of types of cancer diagnosable in said selected body area;

i) selecting a cancer type, from said fourth menu, for which medical information is desired to treat said prospective patient, based on said prospective patient data; and;

j) outputting medical information relating to said selected cancer-type;

k) treating said prospective patient based on said output medical information.

* * * * *